(12) United States Patent
Roberts et al.

(10) Patent No.: US 12,302,814 B2
(45) Date of Patent: *May 20, 2025

(54) *HYDRANGEA MACROPHYLLA* PLANT NAMED BAILMACSEVEN

(71) Applicant: Bailey Nurseries, Inc., Saint Paul, MN (US)

(72) Inventors: David Jonathan Roberts, Athens, GA (US); Justin Alan Schulze, Athens, GA (US); Oren McBee, Bishop, GA (US)

(73) Assignee: Bailey Nurseries, Inc., Saint Paul, MN (US)

( * ) Notice: Subject to any disclaimer, the term of this patent is extended or adjusted under 35 U.S.C. 154(b) by 340 days.

This patent is subject to a terminal disclaimer.

(21) Appl. No.: 17/849,276

(22) Filed: Jun. 24, 2022

(65) Prior Publication Data
US 2023/0413752 A1    Dec. 28, 2023

(51) Int. Cl.
*A01H 5/02* (2018.01)
*A01H 5/10* (2018.01)

(52) U.S. Cl.
CPC ............... *A01H 5/02* (2013.01); *A01H 5/10* (2013.01)

(58) Field of Classification Search
None
See application file for complete search history.

(56) References Cited

U.S. PATENT DOCUMENTS

2022/0095563 A1*   3/2022   Mathey ............... C12Q 1/6895

* cited by examiner

*Primary Examiner* — Vinod Kumar
(74) *Attorney, Agent, or Firm* — Muncy, Geissler, Olds & Lowe, P.C.

(57) ABSTRACT

A new cultivar of *Hydrangea macrophylla* plant named 'Bailmacseven' is disclosed. *Hydrangea macrophylla* variety 'Bailmacseven' is characterized by the new foliage growth that is dark purple in color, the dark purple foliage that retains color throughout the summer into fall even in hot summer climates, the inflorescences with sterile sepals that are red-pink in color with creamy white centers (under non-bluing conditions), and the remontant and heavy blooming habit.

19 Claims, 2 Drawing Sheets
(2 of 2 Drawing Sheet(s) Filed in Color)

HYDRANGEA MACROPHYLLA PLANT NAMED BAILMACSEVEN

FIELD OF DISCLOSURE

The present invention relates to a new and distinct cultivar of *Hydrangea macrophylla* and is referred to hereafter by its cultivar name, 'Bailmacseven'. 'Bailmacseven' represents a new mophead type *Hydrangea*, a deciduous shrub grown for use as a landscape plant.

BACKGROUND OF THE INVENTION

*Hydrangea macrophylla*, commonly referred to as bigleaf hydrangea, is one of the popular landscape shrubs owing to its large mophead flowers. *Hydrangea macrophylla* typically grows 3-6 feet tall and as wide unless damaged by harsh winters or pruned smaller. It generally can produce ball-shaped flower clusters (Mopheads form) or flat clusters of small flowers surrounded by a ring of more prominent flowers (Lacecaps form).

As a landscape plant, retaining the attractive color of a hydrangea is desirable. Some hydrangea plants, including many from European areas, were claimed that the foliage color is retained through the heat of summer even in the more southerly latitudes of the US. However, the color of the new growth hydrangea quickly fades to green and is not retained through the growing season. Accordingly, there exists a need for a hydrangea that retain their color without fading for longer periods of time, especially in hot climates.

The foregoing examples of the related art and limitations related therewith are intended to be illustrative and not exclusive. Other limitations of the related art will become apparent to those of skill in the art upon a reading of the specification.

SUMMARY

It is to be understood that this invention is not limited to particular embodiments described, as such may, of course, vary. The following embodiments and aspects thereof are described in conjunction with systems, tools, and methods which are meant to be exemplary, not limiting in scope.

According to one embodiment, there is provided a plant of *Hydrangea macrophylla* variety 'Bailmacseven' which is valued as breeding line to develop new cultivars of *Hydrangea macrophylla* with dark foliage colors and red or purple mophead flowerheads that retain coloration all season long.

Another embodiment discloses a plant of *Hydrangea macrophylla* variety 'Bailmacseven,' wherein a representative sample of plant tissue cells of said variety has been deposited at the Provasoli-Guillard National Center for Marine Algae and Microbiota (NCMA), located at the Bigelow Laboratory for Ocean Science at 60 Bigelow Drive East Boothbay, ME, 04544, under Accession Number: 202208001.

Another embodiment relates to a plant, or a plant part thereof produced by growing the plant of *Hydrangea macrophylla* variety 'Bailmacseven,' wherein the plant or the plant part comprises at least one cell of *Hydrangea macrophylla* variety 'Bailmacseven'.

Another embodiment relates to a *Hydrangea macrophylla* plant, or part thereof, having all of the physiological and morphological characteristics of the plant of *Hydrangea macrophylla* variety 'Bailmacseven'.

Another embodiment relates to tissue culture produced from protoplasts or cells from the *Hydrangea macrophylla* plants disclosed in the subject application, wherein said cells or protoplasts are produced from a plant part selected from the group consisting of pollen, ovules, embryos, protoplasts, meristematic cells, callus, pollen, leaves, ovules, anthers, cotyledons, hypocotyl, pistils, roots, root tips, flowers, seeds, petiole, and stems.

Another embodiment relates to a *Hydrangea macrophylla* plant regenerated from the tissue or cell culture of 'Bailmacseven'.

Another embodiment relates to a *Hydrangea macrophylla* seed produced by growing the plant of *Hydrangea macrophylla* variety 'Bailmacseven', and a method of producing a *Hydrangea macrophylla* plant, or part thereof, produced by growing the seed.

Another embodiment relates to a method of vegetatively propagating the plant of *Hydrangea macrophylla* variety 'Bailmacseven', comprising the steps of: collecting tissue or cells capable of being propagated from said plant; cultivating said tissue or cells to obtain proliferated shoots; and rooting said proliferated shoots to obtain rooted plantlets; or cultivating said tissue or cells to obtain proliferated shoots, or to obtain plantlets.

A further embodiment relates to a method for producing an embryo or seed, wherein the method comprises crossing the plant of *Hydrangea macrophylla* variety 'Bailmacseven' with another plant and harvesting the resultant embryo or seed. The another plant is a plant of *Hydrangea macrophylla* variety 'Bailmacseven' or a plant of a different *Hydrangea macrophylla* variety.

A further embodiment relates to a method for producing an embryo or seed, comprising further comprising crossing the plant of *Hydrangea macrophylla* variety 'Bailmacseven' with another plant, harvesting the resultant embryo or seed, and producing a plant, or a part thereof, from the resultant embryo or seed.

A further embodiment relates to a *Hydrangea macrophylla* plant produced by cultivating the harvested resultant seed or embryo of a method for producing an embryo or seed.

A further embodiment relates to a method of determining the genotype of the plant of *Hydrangea macrophylla* variety 'Bailmacseven', wherein said method comprises obtaining a sample of nucleic acids from said plant and detecting in said nucleic acids a plurality of polymorphisms.

A further embodiment relates to a method of producing a *Hydrangea macrophylla* plant resistant to the group consisting of herbicides, insecticides, and disease, wherein the method comprises transforming the plant of *Hydrangea macrophylla* variety 'Bailmacseven' with a transgene, and wherein said transgene confers resistance to an herbicide, insecticide, or disease. Another embodiment relates an herbicide, insecticide, or disease resistant plant produced by the method.

A further embodiment relates to a method for developing a *Hydrangea macrophylla* plant in a *Hydrangea macrophylla* plant breeding program, comprising applying plant breeding techniques comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to the *Hydrangea macrophylla* variety 'Bailmacseven', or its parts, wherein application of said techniques results in development of a *Hydrangea macrophylla* plant. A further embodiment relates to a *Hydrangea macrophylla* plant produced by the method.

A further embodiment relates to a method of introducing a mutation into the genome of *Hydrangea macrophylla* variety 'Bailmacseven'; said method comprising mutagenesis of the plant, or plant part thereof, of 'Bailmacseven'; wherein said mutagenesis is selected from the group consisting of temperature, long-term seed storage, tissue culture conditions, ionizing radiation, chemical mutagens, and targeting induced local lesions in genomes, and wherein the resulting plant comprises at least one genome mutation and producing plants therefrom.

A further embodiment relates to a method of editing the genome of *Hydrangea macrophylla* variety 'Bailmacseven,' wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system, and plants produced therefrom.

In addition to the exemplary aspects and embodiments described above, further aspects and embodiments will become apparent by the study of the following descriptions.

BRIEF DESCRIPTION OF THE DRAWINGS

The patent or application file contains at least one drawing and/or photographs executed in color. Copies of this patent or patent application publication with color drawing(s) and/or photograph(s) will be provided by the Patent Office upon request and payment of the necessary fee.

The accompanying color photographs illustrate the overall appearance and distinct characteristics of the new *Hydrangea* plants. The photographs were taken of a 2-year-old plant as grown in a greenhouse in a 2-gallon container in Cottage Grove, Minnesota.

The colors in the photographs may differ slightly from the color values cited in the detailed botanical description, which accurately describe the colors of the new *Hydrangea*.

Figure 1:

FIG. 1 is a color photograph of a view of "Bailmacseven" in bloom.

Figure 2:

FIG. 2 is a color photograph of a view of an inflorescence of "Bailmacseven".

DETAILED DESCRIPTION

Aspects of the invention are disclosed in the following description and related drawings directed to specific embodiments of the invention. Alternate embodiments may be devised without departing from the scope of the invention. Additionally, well-known elements of the invention will not be described in detail or will be omitted so as not to obscure the relevant details of the invention.

*Hydrangea macrophylla* variety 'Bailmacseven' disclosed the present invention is directed to a new and distinct cultivar of *Hydrangea macrophylla*. "Bailmacseven" represents a new mophead type *Hydrangea*, a deciduous shrub grown for use as a landscape plant.

Origin of 'Bailmacseven'

The 'Bailmacseven' was derived from an ongoing breeding program conducted in Winterville, Georgia, the objectives of which are to develop new cultivars of *Hydrangea macrophylla* with dark foliage colors and red or purple mophead flowerheads that retain coloration all season long.

The 'Bailmacseven' comprises a new and distinct variety of *Hydrangea macrophylla* and was created by a controlled cross between unnamed and unpatented proprietary plants from their breeding program accessioned HM16-P4-01 as the female parent and accessioned HM16-R13-02 as the male parent. The 'Bailmacseven' was selected in summer after two years from the pollination as a single unique plant amongst the resulting seedlings.

Asexual propagation of the new cultivar was first accomplished by softwood stem cuttings. Asexual propagation by softwood stem cuttings has determined that the characteristics of the new cultivar are stable and are reproduced true to type in successive generations.

The following traits have been repeatedly observed and represent the characteristics of the new *Hydrangea* cultivar. These attributes in combination distinguish 'Bailmacseven' as a unique cultivar of *Hydrangea*.

(a) The 'Bailmacseven' exhibits new foliage growth that is dark purple in color.
    (b) The 'Bailmacseven' exhibits dark purple foliage that retains color throughout the summer into fall even in hot summer climates.
    (c) The 'Bailmacseven' exhibits inflorescences with sterile sepals that are red-pink in color with creamy white centers (under non-bluing conditions).
    (d) The 'Bailmacseven' exhibits heavy blooming habit.

The female parent of the 'Bailmacseven' differs from the 'Bailmacseven' in having foliage that is dark green in color with purple highlights and inflorescences with sterile sepals that are pink in color. The male parent of the 'Bailmacseven' differs from the 'Bailmacseven' in having foliage that is dark green in color with purple highlights, a smaller plant size, and lacecap inflorescences with sterile sepals that are pink in color. The 'Bailmacseven' can be most closely compared to the *Hydrangea macrophylla* cultivars the 'Hokomabebos' (U.S. Plant application Ser. No. 17/372,452) and the 'Jon04' (U.S. Plant Pat. No. 30,453). The 'Hokomabebos' and the 'Jon04' are both similar to the 'Bailmacseven' in having mophead type flowers and new growth that is purple in color. The 'Hokomabebos' differs from the 'Bailmacseven' in having foliage that turns green with purple highlights in summer, inflorescences with sterile sepals that are lighter red-pink in color, and a shorter stem internode length. The 'Jon04' differs from the 'Bailmacseven' in having foliage that turns to dark green with purple highlights in summer, inflorescences with sterile sepals that are lighter red-pink in color, and a shorter stem internode length.

Detailed Botanical Description of the 'Bailmacseven'

The following is a detailed description of 2-year-old plants of the 'Bailmacseven' as grown outdoors in 2-gallon containers in a greenhouse in Cottage Grove, Minnesota. The plants were grown under non-blueing conditions. Plants are not being grown under blueing conditions however limited sterile sepal color is provided as recorded from a trial. The phenotype of the new cultivar may vary with variations in environmental, climatic, and cultural conditions, as it has not been tested under all possible environmental conditions. The color determination is in accordance with the 2015 Colour Chart of the Royal Horticultural Society, London, England, except where general color terms of ordinary dictionary significance are used.

General Description:
    Blooming period—4 weeks in June in Georgia.
    Plant type—Deciduous shrub, mophead type *Hydrangea*.
    Plant habit—Upright mounded.
    Height and spread—Reaches about 46 cm in height and 70 cm in spread as grown in a 2-gallon container, reaches reaching 91 cm to 121 cm in height and width as grown in the landscape in Georgia.
    Hardiness—At least in U.S.D.A. Zones 5 to 9.
    Diseases—Resistance to powdery mildew (*Podosphaera macularis*) and leafspot (*Cercospora hydrangea*).

Root description—Fine and fibrous, 199B in color.
Propagation—Softwood stem cuttings.
Growth rate—Moderate.
Root development—Softwood cuttings root readily in 6 weeks, rooted cuttings are overwintered and roots will fully develop in a one-quart container by mid-summer the following year.

Stem Description:
  Stem shape—Rounded.
  Stem strength—Strong.
  Stem color—Young; 145A, mature; 165B.
  Stem size—Main branches; average of 19 cm in length, 1 cm in diameter, lateral branches; average of 30 cm in length, 5 mm in diameter.
  Stem surface—Younger and mature stems; glabrous, sparsely to moderately lenticellate, lenticles; 5 per cm$^2$, an average of 1.5 mm in length and 0.5 mm in width, N92A in color, old growth at base; bark-like, rugose, slightly fascinated, 165A in color.
  Internode length—Average of 8 cm.
  Branching—Average of 5 main branches, average of 3 to 5 lateral branches per main branch.
  Stipules—Persistent, 2 opposite at base of petioles, stipule bud; is 2 mm in length, 1 mm in width, 79A in color, oblong in shape, acute apex, glossy and glabrous surface.

Foliage Description:
  Leaf shape—Elliptical.
  Leaf arrangement—Opposite.
  Leaf division—Simple.
  Leaf base—Attenuate.
  Leaf apex—Apiculate.
  Leaf margins—Serrate.
  Leaf venation—Pinnate, upper surface; 142A, lower surface; 142D, flushed with 187A in color.
  Leaf size—Average of 14 cm in length and 6.5 cm in width.
  Leaf attachment—Petiolate.
  Leaf surface—Upper surface; glossy, lower surface; matte.
  Leaf color—Young upper surface; N186A, mature upper surface; 202A, young and mature lower surface; a blend of 197A and N189B.
  Petioles—An average of 3 cm in length and 3 mm in diameter, young upper surface color 146A, young lower surface color 138A flushed with 183A, mature upper and lower surface 144A, both surfaces glabrous and glossy.

Inflorescence Description:
  Inflorescence typ.—Terminal panicle, full rounded mophead in form, comprised of fertile flowers and single sterile flowers.
  Lastingness of inflorescence—Persistent for 3 months.
  Inflorescence number—One per lateral.
  Inflorescence size—Average of 16 cm in height, 17 cm in diameter.
  Flower number—Average of 120 sterile flowers and 27 fertile flowers per panicle.
  Flower fragrance—Very faint, floral rose fragrance.
  Flower aspect—Upright to outward.
  Flower size—Sterile flowers; an average of 3.2 cm in diameter, 1 cm in depth, fertile flowers; do not open.
  Flower type—Rotate.
  Flower buds—Sterile flowers; average of 5 mm in length and 3 mm in diameter, oblong, flattened in shape, color when young; top N79A, mid-section 71A, base 8D, color when mature top 79A, mid-section 62A, base N155C, fertile flowers; average of 3 mm in width and depth, obovate in shape, color when young; a blend of 187A and 46A, color when mature; top N92A, base 62D.
  Peduncles—Moderately strong, average of 1.2 cm in length and 2 mm in width, color; a blend of 59A and NN155A, surface is matte, rugose and moderately covered with very minute woolly hairs that matches surface color to NN155A in color.
  Pedicels—Moderately strong, average of 8 mm in length and 1 mm in width, color; young pedicels N92A, mature pedicels ranging between 157A and 142B in color, occasionally speckled with 71A in color, surface is matte and moderately covered with very fine woolly hairs that match surface color or NN155A in color.
  Petals—Sterile flowers; petals do not fully open, petal spot 1.5 mm in diameter and N92A in color when mature, fertile flowers; petals do not fully open, N92A in color as a flower bud.
  Sepals—Sterile flowers; showy, 3 to 4, deltoid to reniform in shape, moderately to strongly overlapping, rotate in arrangement, serrate and crenate margins moderately undulate, apex is very slightly retuse to bluntly pointed, cuneate base, average of 1.7 cm in length and 1.9 cm in width, upper and lower surface glabrous and satiny, color: when opening upper and lower surface; base, center and veins N144A, outside edges 187A to 187B, when fully open upper surface; base, center and veins NN155C, flushed with 145A, outside edges 67A, margins 71A, when fully open lower surface; base NN155C, very lightly flushed with 145A, center 68B to 68C, margins 71A, fertile flowers; do not open, 62A in color and fused into *campanula* shape as a flower bud, color when fully open upper surface under blueing conditions; a blend of N8OB and NN155C, margins N80A, base (centers) NN155C.

Reproductive Organs:
  Presence—Not observed; fertile flowers drop when mature, gynoecium and androecium not developed.
  Fruit and seed—Not observed.

The new 'Bailmacseven' variety has not been observed under all possible environmental conditions to date. Accordingly, it is possible that the phenotypic expression may vary somewhat with changes in light intensity and duration, cultural practices, and other environmental conditions.

Breeding with *Hydrangea macrophylla* Variety 'Bailmacseven'

The goal of *Hydrangea macrophylla* breeding is to develop new and superior *Hydrangea macrophylla* varieties and hybrids. The breeder initially selects and crosses two or more parental varieties, followed by repeated selfing and selection, producing many new genetic combinations. The breeder can theoretically generate billions of different genetic combinations via crossing, selection, selfing, and mutagenesis.

Due to the large number of possible genetic combinations that result from such a cross, it is often difficult to reproduce a variety with a particular desired trait by simply crossing the same original parents and utilizing the same selection techniques. This unpredictability results in the expenditure of large amounts of research funds to develop superior *Hydrangea macrophylla* varieties. To advance breeding programs more quickly, breeders often use a variety that contains the desired trait as a parental line as a starting point rather than trying to recreate the variety possessing that desired trait.

Breeding programs combine desirable traits from two or more varieties or various broad-based sources into breeding pools from which varieties are developed and selected for desired phenotypes. Breeding programs may include artificial pollination wherein two parents are crossed which previously had been studied in the hope that the parents would contribute the desired characteristics. Seeds resulting from such artificial pollination can be sown to obtain small plants, and then the selective study can be used to identify a new plant variety which includes the desired phenotype.

Pedigree breeding is commonly used for the improvement of self-pollinating plants. An example of pedigree breeding is when two parents that possess favorable traits are crossed to produce an $F_1$. Then an $F_2$ population is produced by selfing one or several $F_{1s}$. This is followed by a selection of the best individuals which may begin in the $F_2$ population; then, often beginning in the $F_3$, the best individuals in the best families are selected. Replicated testing of families may often begin in the $F_4$ generation to improve the effectiveness of a selection for traits with low heritability. At an advanced stage of inbreeding, the best lines or mixtures of phenotypically similar lines may be further tested for a selection of new varieties.

Using *Hydrangea macrophylla* variety 'Bailmacseven' to Develop Other *Hydrangea macrophylla* Varieties

*Hydrangea macrophylla* varieties such as *Hydrangea macrophylla* variety 'Bailmacseven' are a source of breeding material that may be used to develop new *Hydrangea macrophylla* varieties. Plant breeding techniques known in the art and used in a *Hydrangea macrophylla* breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, transformation, and gene editing. These techniques can be used singularly or in combinations. There are many analytical methods available to evaluate a new variety. The oldest and most traditional method of analysis is the observation of phenotypic traits, but genotypic analysis may also be used.

Additional Breeding Methods

Any plants produced using the 'Bailmacseven' plants disclosed in the present application as at least one parent are also an embodiment. Thus, plants which contain about 50% of the genetic composition of 'Bailmacseven' are another embodiment of the present invention. Methods for producing progeny using 'Bailmacseven' as at least one of the parents are well-known in the art and some of the more commonly used breeding methods are described herein. Descriptions of exemplary breeding methods can be found in published reference books (e.g., Allard, "Principles of Plant Breeding" (1999); and Vainstein, "Breeding for Ornamentals: Classical and Molecular Approaches," Kluwer Academic Publishers (2002); Callaway, "Breeding Ornamental Plants," Timber Press (2000).

Breeding steps that may be used in the *Hydrangea macrophylla* variety 'Bailmacseven' plant breeding program can include, for example, artificial pollination using 'Bailmacseven' as at least one of the parents, pedigree breeding, backcrossing, mutation breeding, and recurrent selection. In conjunction with these steps, techniques such as RFLP-enhanced selection, genetic marker enhanced selection (for example, SSR markers), Gene Editing and the making of double haploids may be utilized.

As used herein, the term "plant" or plant part includes plant cells, plant protoplasts, plant cell tissue cultures from which 'Bailmacseven' plants can be regenerated, plant calli, plant clumps, and plant cells that are intact in plants or parts of plants, such as pollen, ovules, embryos, protoplasts, meristematic cells, callus, pollen, leaves, ovules, anthers, cotyledons, hypocotyl, pistils, roots, root tips, seeds, flowers, petiole, pods, shoot, or stems and the like.

Pedigree Breeding

Pedigree breeding starts with the crossing of two genotypes, such as *Hydrangea macrophylla* variety 'Bailmacseven' and another *Hydrangea macrophylla* variety having one or more desirable characteristics that is lacking or which complements *Hydrangea macrophylla* variety 'Bailmacseven'. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

Backcross Breeding

Backcross breeding has been used to transfer genes for a simply inherited, highly heritable trait into a desirable homozygous variety or inbred variety which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., variety) and the desirable trait transferred from the donor parent. This is also known as single gene conversion and/or backcross conversion.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good commercial characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. As used herein, progeny refers to the descendants of one or more of the parental lines and includes an $F_1$ *Hydrangea macrophylla* plant produced from the cross of two *Hydrangea macrophylla* plants where at least one plant includes a *Hydrangea macrophylla* plant disclosed herein and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line. For example, a *Hydrangea macrophylla* plant may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new *Hydrangea macrophylla* varieties.

Therefore, another embodiment is a method of making a backcross conversion of *Hydrangea macrophylla* variety 'Bailmacseven', comprising the steps of crossing *Hydrangea macrophylla* variety 'Bailmacseven' with a donor plant comprising a desired trait, selecting an $F_1$ progeny plant comprising the desired trait, and backcrossing the selected $F_1$ progeny plant to *Hydrangea macrophylla* variety 'Bailmacseven'. This method may further comprise the step of obtaining a molecular marker profile of *Hydrangea macrophylla* variety 'Bailmacseven' and using the molecular marker profile to select for a progeny plant with the desired trait and the molecular marker profile of *Hydrangea macrophylla* variety 'Bailmacseven'.

Recurrent Selection and Mass Selection

Recurrent selection is a method used in a plant breeding program to improve a population of plants. *Hydrangea macrophylla* variety 'Bailmacseven' is suitable for use in a recurrent selection program. The method entails individual plants cross pollinating with each other to form progeny. The progeny are grown and the superior progeny selected by any number of selection methods, which include individual plant, half-sib progeny, full-sib progeny, and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating crops. A genetically variable population of heterozygous individuals is either identified, or created, by intercrossing several different parents. The plants are selected based on individual superiority, outstanding progeny, or excellent combining ability. The selected plants are intercrossed to produce a new population in which further cycles of selection are continued.

Protoplast Fusion

Also known as somatic fusion, this process can be used with 'Bailmacseven' to create hybrids. The resulting hybrid plants have the chromosomes of each parent and thus the process is useful for incorporating new traits. The protoplast fusion technique is well known in the art; see, for example, Hamill J. D., Cocking E. C. (1988) Somatic Hybridization of Plants and its Use in Agriculture. In: Pais M. S. S., Mavituna F., Novais J. M. (eds) Plant Cell Biotechnology. NATO ASI Series (Series H: Cell Biology), vol 18.

Essentially Derived Varieties

An essentially derived variety is predominantly derived from the initial variety, or from a variety that is itself predominantly derived from the initial variety, while retaining the expression of the essential characteristics that result from the genotype or combination of genotypes of the initial variety; is clearly distinguishable from the initial variety; and except for the differences which result from the act of derivation, it conforms essentially to the initial variety in the expression of the essential characteristics that result from the genotype or combination of genotypes of the initial variety. An essentially derived variety may be obtained by the selection of a natural mutant (e.g., spontaneous mutant, also referred to as a sport) or induced mutant or of a somaclonal variant, the selection of a variant individual from plants of the initial variety, backcrossing, transformation by genetic engineering, or other methods.

Therefore, another embodiment is to an essentially derived variety of 'Bailmacseven'. A further embodiment is to a methods of artificially inducing an essentially derived variety from 'Bailmacseven'.

Mutation Breeding

Mutation breeding is another method of introducing new traits into *Hydrangea macrophylla* variety 'Bailmacseven'. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, ionizing radiation, such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm); chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates such as ethyl methanesulfonate, sulfones, lactones), sodium azide, hydroxylamine, nitrous acid, methylnitrilsourea, or acridines; TILLING (targeting induced local lesions in genomes), where mutation is induced by chemical mutagens and mutagenesis is accompanied by the isolation of chromosomal DNA from every mutated plant line or seed and screening of the population of the seed or plants is performed at the DNA level using advanced molecular techniques. Once a desired trait is observed through mutagenesis the trait may then be incorporated into existing germplasm by traditional breeding techniques.

Details of mutation breeding can be found, for example, in Vainstein, "Breeding for Ornamentals: Classical and Molecular Approaches," Kluwer Academic Publishers (2002); Sikora, Per, et al., "Mutagenesis as a Tool in Plant Genetics, Functional Genomics, and Breeding" International Journal of Plant Genomics. 2011 (2011); 13 pages. In addition, mutations created in other *Hydrangea macrophylla* plants may be used to produce a backcross conversion of *Hydrangea macrophylla* that comprises such mutation.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues of 'Bailmacseven' by using either microprojectile-mediated delivery with a biolistic device or by using *Agrobacterium*-mediated transformation. Transformant plants obtained with the protoplasm of the embodiments are intended to be within the scope of the embodiments.

Gene Editing Using CRISPR

Targeted gene editing can be done using CRISPR/Cas9 technology (Saunders & Joung, Nature Biotechnology, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. J. Bacteriol. 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. Science 315, 1709-1712 (2007). Many plants have already been modified using the CRISPR system. See, for example, Zhang, B. et al., "Exploiting the CRISPR/Cas9 System for Targeted Genome Mutagenesis in *Petunia*" Science Reports, Vol. 6, February 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., Annu. Rev. Biochem. 82:273-266, 2013; and Wang, S. et al., Plant Cell Rep (2015) 34: 1473-1476.

Therefore, it is another embodiment to use the CRISPR system on *Hydrangea macrophylla* variety 'Bailmacseven' to modify traits and resistances or tolerances to pests, herbicides, and viruses.

Gene Editing Using TALENs

Transcription activator-like effector nucleases (TALENs) have been successfully used to introduce targeted mutations via repair of double stranded breaks (DSBs) either through non-homologous end joining (NHEJ), or by homology-directed repair (HDR) and homology-independent repair in the presence of a donor template. Thus, TALENs are another mechanism for targeted genome editing using 'Bailmacseven'. The technique is well known in the art; see, for example, Malzahn, Aimee et al. "Plant genome editing with TALEN and CRISPR" Cell & bioscience vol. 7 21. 24 Apr. 2017.

Therefore, it is another embodiment to use the TALENs system on *Hydrangea macrophylla* variety 'Bailmacseven' to modify traits and resistances or tolerances to pests, herbicides, and viruses.

Other Methods of Genome Editing

In addition to CRISPR and TALENs, two other types of engineered nucleases can be used for genome editing: engineered homing endonucleases/meganucleases (EMNs), and zinc finger nucleases (ZFNs). These methods are well known in the art. See, for example, Petilino, Joseph F. "Genome editing in plants via designed zinc finger nucleases" In Vitro Cell Dev Biol Plant. 51(1): pp. 1-8 (2015); and Daboussi, Fayza, et al. "Engineering Meganuclease for Precise Plant Genome Modification" in Advances in New Technology for Targeted Modification of Plant Genomes. Springer Science+Business. pp 21-38 (2015).

Therefore, it is another embodiment to use engineered nucleases on *Hydrangea macrophylla* variety 'Bailmacseven' to modify traits and resistances or tolerances to pests, herbicides, and viruses.

Gene Silencing

Techniques for gene silencing are well-known in the art, including, but not limited to, knock-outs (such as by insertion of a transposable element such as Mu) or other genetic elements such as a FRT, Lox, or other site specific integration sites; antisense technology; co-suppression; RNA interference; virus-induced gene silencing; target-RNA-specific ribozymes; hairpin structures; MicroRNA; ribozymes; oligonucleotide mediated targeted modification; Zn-finger targeted molecules; CRISPR/Cas9 system; and other methods or combinations of the above methods known to those of skill in the art. See, e.g., Sheehy, et al., PNAS USA, 85:8805-8809 (1988); U.S. Pat. Nos. 5,107,065; 5,453,566; 5,759,829; Jorgensen, TRENDS BIOTECH., 8(12):340-344 (1990); Flavell, PNAS USA, 91:3490-3496 (1994); Neuhuber, et al., MOL. GEN. GENET., 244:230-241 (1994); Napoli, et al., PLANT CELL, 2:279-289 (1990); U.S. Pat. No. 5,034,323; Sharp, GENES DEV., 13:139-141 (1999); Zamore, et al., CELL, 101:25-33 (2000); Montgomery, et al., PNAS USA, 95:15502-15507 (1998); Burton, et al., PLANT CELL, 12:691-705 (2000); Baulcombe, CURR. OP. PLANT BIO., 2:109-113 (1999); Haseloff, et al., NATURE, 334:585-591 (1988); Smith, et al., NATURE, 407:319-320 (2000); U.S. Pat. Nos. 6,423,885; 7,138,565; 6,753,139; 7,713,715; Aukerman & Sakai, PLANT CELL, 15:2730-2741 (2003); Steinecke, et al., EMBO J., 11:1525 (1992); Perriman, et al., ANTISENSE RES. DEV., 3:253 (1993); U.S. Pat. Nos. 6,528,700; 6,911,575; 7,151,201; 6,453,242; 6,785,613; 7,177,766; 7,788,044; International Publication No. WO2014/068346; Martinelli, et al., Proposal of a Genome Editing System for Genetic Resistance to Tomato Spotted Wilt Virus 2014 AMERICAN JOURNAL OF APPLIED SCIENCES; Noman, et al., CRISPR-Cas9: Tool for Qualitative and Quantitative Plant Genome Editing, November 2016 FRONTIERS IN PLANT SCIENCE Vol. 7; and Zhang et al., Exploiting the CRISPR/Cas9 System for Targeted Genome Mutagenesis in *Petunia* February 2016 SCIENCE REPORTS Volume 6.

Introduction of a New Trait or Locus into *Hydrangea macrophylla* variety 'Bailmacseven'

*Hydrangea macrophylla* variety 'Bailmacseven' represents a new base of genetics into which a new locus or trait may be introgressed or introduced. Direct transformation and backcrossing represent two important methods that can be used to accomplish such an introgression. The term backcross conversion and single locus conversion are used interchangeably to designate the product of a backcrossing program.

Molecular Techniques Using *Hydrangea macrophylla* Variety 'Bailmacseven'

The advent of new molecular biological techniques has allowed the isolation and characterization of genetic elements with specific functions. Traditional plant breeding has principally been the source of new germplasm, however, advances in molecular technologies have allowed breeders to provide varieties with novel and much wanted commercial attributes. Molecular techniques such as transformation are popular in breeding ornamental plants and well-known in the art. See e.g., Vainstein, "Breeding for Ornamentals: Classical and Molecular Approaches," Kluwer Academic Publishers (2002).

Breeding with Molecular Markers

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses. Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing *Hydrangea macrophylla* Variety 'Bailmacseven'. See Vainstein, "Breeding for Ornamentals: Classical and Molecular Approaches," Kluwer Academic Publishers (2002).

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See, for example, Fletcher, Richard S., et al., "QTL analysis of root morphology, flowering time, and yield reveals trade-offs in response to drought in *Brassica napus* Journal of Experimental Biology. 66 (1): 245-256 (2014). QTL markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a *Hydrangea macrophylla* plant for which *Hydrangea macrophylla* Variety 'Bailmacseven' is a parent can be used to produce double haploid plants. Double haploids are produced by the doubling of a set of chromosomes (1N) from a heterozygous plant to produce a completely homozygous individual. This can be advantageous because the process omits the generations of selfing needed to obtain a homozygous plant from a heterozygous source. For example, see, Ferrie, Alison M. R., et al., "Review of Doubled Haploidy Methodologies in Ornamental Species" Propagation of Ornamental Plants. 11(2): pp. 63-77 (2011).

Thus, an embodiment is a process for making a substantially homozygous *Hydrangea macrophylla* Variety 'Bailmacseven' progeny plant by producing or obtaining a seed from the cross of *Hydrangea macrophylla* Variety 'Bailmacseven' and another *Hydrangea macrophylla* plant and applying double haploid methods to the $F_1$ seed or $F_1$ plant or to any successive filial generation.

In particular, a process of making seed retaining the molecular marker profile of *Hydrangea macrophylla* Variety 'Bailmacseven' is contemplated, such process comprising obtaining or producing $F_1$ seed for which *Hydrangea macrophylla* Variety 'Bailmacseven' is a parent, inducing doubled haploids to create progeny without the occurrence of meiotic segregation, obtaining the molecular marker profile of *Hydrangea macrophylla* Variety 'Bailmacseven', and selecting progeny that retain the molecular marker profile of *Hydrangea macrophylla* Variety 'Bailmacseven'.

Expression Vectors for *Hydrangea macrophylla* Transformation: Marker Genes

Plant transformation involves the construction of an expression vector which will function in plant cells. Such a vector comprises DNA comprising a gene under control of, or operatively linked to, a regulatory element (for example, a promoter). Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well-known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Another commonly used selectable marker gene is the hygromycin phosphotransferase gene which confers resistance to the antibiotic hygromycin.

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., Somatic Cell Mol. Genet., 13:67 (1987); Shah, et al., Science, 233:478 (1986); Charest, et al., Plant Cell Rep., 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used marker genes for screening presumptively transformed cells include β-glucuronidase (GUS), β-galactosidase, luciferase, and chloramphenicol acetyltransferase (Jefferson, R. A., Plant Mol. Biol. Rep., 5:387 (1987); Teeri, et al., EMBO J., 8:343 (1989); Koncz, et al., Proc. Natl. Acad. Sci. USA, 84:131 (1987); DeBlock, et al., EMBO J., 3:1681 (1984)).

Expression Vectors for *Hydrangea macrophylla* Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions. Many types of promoters are well known in the art.

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized. Many signal sequences are well-known in the art. See, for example, Becker, et al., Plant Mol. Biol., 20:49 (1992); Knox, C., et al., *Plant Mol. Biol.,* 9:3-17 (1987); Lerner, et al., Plant Physiol., 91:124-129 (1989); Frontes, et al., Plant Cell, 3:483-496 (1991); Matsuoka, et al., Proc. Natl. Acad. Sci., 88:834 (1991); Gould, et al., J. Cell. Biol., 108:1657 (1989); Creissen, et al., Plant J., 2:129 (1991); Kalderon, et al., Cell, 39:499-509 (1984); Steifel, et al., Plant Cell, 2:785-793 (1990).

Foreign Protein Genes: Transformation

Various promoters, targeting sequences, enhancing sequences, and other DNA sequences can be inserted into the genome for the purpose of altering the expression of genes.

Many techniques for altering gene expression are well-known to one of skill in the art, including, but not limited to, knock-outs (such as by insertion of a transposable element such as Mu (Vicki Chandler, The Maize Handbook, Ch. 118 (Springer-Verlag 1994)) or other genetic elements such as a FRT, Lox, or other site specific integration sites; antisense technology (see, e.g., Sheehy, et al., PNAS USA, 85:8805-8809 (1988) and U.S. Pat. Nos. 5,107,065, 5,453,566, and 5,759,829); co-suppression (e.g., Taylor, Plant Cell, 9:1245 (1997); Jorgensen, Trends Biotech., 8(12):340-344 (1990); Flavell, PNAS USA, 91:3490-3496 (1994); Finnegan, et al., Bio/Technology, 12:883-888 (1994); Neuhuber, et al., Mol. Gen. Genet., 244:230-241 (1994)); RNA interference (Napoli, et al., Plant Cell, 2:279-289 (1990); U.S. Pat. No. 5,034,323; Sharp, Genes Dev., 13:139-141 (1999); Zamore, et al., Cell, 101:25-33 (2000); Montgomery, et al., PNAS USA, 95:15502-15507 (1998)), virus-induced gene silencing (Burton, et al., Plant Cell, 12:691-705 (2000); Baulcombe, Curr. Op. Plant Bio., 2:109-113 (1999)); target-RNA-specific ribozymes (Haseloff, et al., Nature, 334:585-591 (1988)); hairpin structures (Smith, et al., Nature, 407: 319-320 (2000); U.S. Pat. Nos. 6,423,885, 7,138,565, 6,753, 139, and 7,713,715); MicroRNA (Aukerman & Sakai, Plant Cell, 15:2730-2741 (2003)); ribozymes (Steinecke, et al., EMBO J., 11:1525 (1992); Perriman, et al., Antisense Res. Dev., 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); transposable elements (e.g. Dubin, M. J., et al., Transposons: a blessing curse, Current opinion in plant biology, Vol: 42, Page: 23-29, 2018 and Eric T. Johnson, Jesse B. Owens & Stefan Moisyadi (2016) Vast potential for using the piggy-Bac transposon to engineer transgenic plants at specific genomic locations, Bioengineered, 7:1, 3-6) and other methods or combinations of the above methods known to those of skill in the art.

The foregoing methods for transformation may be used for producing a transgenic variety. The transgenic variety could then be crossed with another (non-transformed or transformed) variety in order to produce a new transgenic variety. Alternatively, a genetic trait that has been engineered into a particular *Hydrangea macrophylla* variety using the foregoing transformation techniques could be moved into another variety using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Likewise, by means of one embodiment, genes can be expressed in transformed plants. More particularly, plants can be genetically engineered to express various phenotypes of interest, including, but not limited to, genes that confer resistance to pests or disease, genes that confer resistance to an herbicide, genes that confer or contribute to a value-added or desired trait, genes that control male sterility, genes that create a site for site specific DNA integration, and genes that affect abiotic stress resistance. Many hundreds if not thousands of different genes are known and could potentially be introduced into a plant according to the invention. Non-limiting examples of particular genes and corresponding phenotypes one may choose to introduce into a plant include one or more genes for insect tolerance, such as a *Bacillus thuringiensis* (Bt.) gene, pest tolerance such as genes for fungal disease control, herbicide tolerance such as genes conferring glyphosate tolerance, and genes for quality improvements such as, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety. Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev., 9:207, 1991). The RNA could also be a catalytic RNA molecule (i.e., a ribozyme) engineered to cleave a desired endogenous mRNA product (see, for example, Gibson and Shillito, Mol. Biotech., 7:125, 1997). Thus, any gene which produces a protein or mRNA which expresses a phenotype or morphology change of interest is useful for the practice of one or more embodiments.

Tissue Culture

Further reproduction of the variety can occur by tissue culture and regeneration. Tissue culture of various tissues of ornamental plants and *Hydrangea macrophylla* Variety 'Bailmacseven' and regeneration of plants therefrom is well-known and widely published. For example, reference may be had to Valla Rego, Luciana et al., Crop Breeding and Applied Technology. 1(3): 283-300 (2001); Komatsuda, T., et al., Crop Sci., 31:333-337 (1991); Stephens, P. A., et al., Theor. Appl. Genet., 82:633-635 (1991); Komatsuda, T., et al., *Plant Cell, Tissue and Organ Culture,* 28:103-113 (1992); Dhir, S., et al., Plant Cell Reports, 11:285-289 (1992); Pandey, P., et al., Japan J. Breed., 42:1-5 (1992); and Shetty, K., et al., Plant Science, 81:245-251 (1992). Thus, another embodiment is to provide cells which upon growth and differentiation produce *Hydrangea macrophylla* plants having the physiological and morphological characteristics of *Hydrangea macrophylla* Variety 'Bailmacseven' described in the present application.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One or more aspects may be embodied in other specific forms without departing from its spirit or essential characteristics. The described embodiments are to be considered in all respects only as illustrative and not restrictive. The scope of the embodiments is, therefore, indicated by the appended claims rather than by the foregoing description. All changes which come within the meaning and range of equivalency of the claims are to be embraced within their scope. The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the claimed embodiments require more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice of one or more embodiments.

Deposit Information

Under the provisions of the Budapest Treaty on the International Recognition of the Deposit of Microorganisms for the Purpose of Patent Procedure, Applicant has deposited biological material comprising *Hydrangea macrophylla* Variety 'Bailmacseven' plant tissue cells disclosed above and recited in the appended claims at the Provasoli-Guillard National Center for Marine Algae and Microbiota (NCMA), located at the Bigelow Laboratory for Ocean Science at 60 Bigelow Drive East Boothbay, ME, 04544, under Accession Number: 202208001 on Aug. 10, 2022.

The invention claimed is:

1. A plant, or a plant part thereof produced by growing a plant of *Hydrangea macrophylla* variety 'Bailmacseven,' wherein a representative sample of plant tissue cells of said variety is deposited at NCMA under Accession Number: 202208001, and wherein the plant or the plant part comprises at least one cell of *Hydrangea macrophylla* variety 'Bailmacseven'.

2. A *Hydrangea macrophylla* plant, or part thereof, having all of the physiological and morphological characteristics of the plant of claim 1.

3. A tissue or cell culture of regenerable cells produced from the plant of claim 1.

4. The tissue or cell culture of claim 3, comprising tissues or cells from a plant part selected from the group consisting of leaves, pollen, embryos, cotyledons, hypocotyl, meristematic cells, roots, root tips, pistils, anthers, flowers, and stems.

5. A *Hydrangea macrophylla* plant regenerated from the tissue or cell culture of claim 3, wherein said plant has all of the morphological and physiological characteristics of the plant of the *Hydrangea macrophylla* variety 'Bailmacseven'.

6. A method of vegetatively propagating the plant of claim 1, comprising the steps of:
collecting tissue or cells capable of being propagated from said plant;
cultivating said tissue or cells to obtain proliferated shoots; and
rooting said proliferated shoots to obtain rooted plantlets; or cultivating said tissue or cells to obtain proliferated shoots, or to obtain plantlets.

7. A method for producing a resultant embryo or seed, wherein the method comprises crossing the plant of claim 1 with another plant and harvesting the resultant embryo or seed.

8. The method of claim 7, wherein said another plant is a plant of *Hydrangea macrophylla* variety 'Bailmacseven'.

9. The method of claim 7, wherein said another plant is a plant of a different *Hydrangea macrophylla* variety.

10. The method of claim 7, further comprising producing a plant, or a part thereof, from the resultant embryo or seed.

11. A *Hydrangea macrophylla* plant produced by cultivating the harvested resultant seed or embryo produced by the method of claim 7, wherein said *Hydrangea macrophylla* plant has all of the morphological and physiological characteristics of said *Hydrangea macrophylla* variety 'Bailmacseven'.

12. A method of determining the genotype of the *Hydrangea macrophylla* plant of claim 1, wherein said method comprises obtaining a sample of nucleic acids from said plant and detecting in said nucleic acids a plurality of polymorphisms.

13. A method of producing a *Hydrangea macrophylla* plant variety 'Bailmacseven' resistant to an herbicide, an insecticide, or a disease, comprising transforming the *Hydrangea macrophylla* plant variety 'Bailmacseven' of claim 1 with a transgene, wherein expression of the transgene in said *Hydrangea macrophylla* plant variety 'Bailmacseven' results in an increase in resistance to the herbicide, the insecticide, or the disease.

14. An herbicide, an insecticide, or disease resistant plant produced by the method of claim 13, wherein the resistant plant otherwise has all of the physiological and morphological characteristics of *Hydrangea macrophylla* variety 'Bailmacseven', and wherein a representative sample of plant tissue cells of said variety is deposited at NCMA under Accession Number: 202208001.

15. A method for developing a *Hydrangea macrophylla* plant in a plant breeding program, comprising applying plant breeding techniques comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to a plant of *Hydrangea macrophylla* variety 'Bailmacseven,' wherein a representative sample of plant tissue cells of 'Bailmacseven' is deposited at NCMA under Accession Number: 202208001, wherein application of said techniques results in development of a *Hydrangea macrophylla* plant.

16. A *Hydrangea macrophylla* plant produced by the method of claim 15, wherein the *Hydrangea macrophylla* plant has all of the physiological and morphological characteristics of *Hydrangea macrophylla* variety 'Bailmacseven', and wherein a representative sample of plant tissue cells of said variety is deposited at NCMA under Accession number:202208001.

17. A method of introducing a mutation into the genome of *Hydrangea macrophylla* variety 'Bailmacseven', said method comprising mutagenesis of the plant, or plant part thereof, of claim 1, wherein said mutagenesis comprises temperature conditions, long-term seed storage conditions, tissue culture conditions, ionizing radiation, chemical mutagens, or targeting induced local lesions in genomes, and wherein the resulting plant comprises at least one genome mutation.

18. A method of editing the genome of *Hydrangea macrophylla* variety 'Bailmacseven', said method comprising editing the genome of the plant, or plant part thereof, of a plant of *Hydrangea macrophylla* variety 'Bailmacseven', wherein a representative sample of plant tissue cells of said variety 'Bailmacseven' is deposited at NCMA under Accession Number: 202208001, wherein said editing comprising zinc finger nucleases, transcription activator-like effector nucleases (TALENs), engineered homing endonucleases or meganucleases, or clustered regularly interspaced short palindromic repeat (CRISPR)-associated protein9 (Cas9) system.

19. A method for developing a *Hydrangea macrophylla* variety, comprising one or more of:
a) identifying and selecting a spontaneous mutation of a plant of *Hydrangea macrophylla* variety 'Bailmacseven' or a part thereof, and cultivating said selected spontaneous mutation plant or plant part;
b) introducing a mutation into the genome of a plant of *Hydrangea macrophylla* variety 'Bailmacseven' or a part thereof, and cultivating said mutated plant or plant part; or
c) transforming a plant of *Hydrangea macrophylla* variety 'Bailmacseven' with a transgene; wherein a representative sample of plant tissue cells of said variety 'Bailmacseven' of parts a), b) and c) is deposited at NCMA under Accession Number: 202208001.

* * * * *